(12) United States Patent
Ishikawa

(10) Patent No.: US 7,309,873 B2
(45) Date of Patent: Dec. 18, 2007

(54) RAINDROP SENSOR

(75) Inventor: Junichi Ishikawa, Kariya (JP)

(73) Assignee: Denso Corporation (JP)

( * ) Notice: Subject to any disclaimer, the term of this patent is extended or adjusted under 35 U.S.C. 154(b) by 90 days.

(21) Appl. No.: 11/213,851

(22) Filed: Aug. 30, 2005

(65) Prior Publication Data

US 2006/0043322 A1    Mar. 2, 2006

(30) Foreign Application Priority Data

Sep. 2, 2004    (JP) .............................. 2004-255971

(51) Int. Cl.
*G01N 21/49* (2006.01)
(52) U.S. Cl. ...................... 250/574; 250/573
(58) Field of Classification Search ........... 250/227.25, 250/573–575; 340/602
See application file for complete search history.

(56) References Cited

U.S. PATENT DOCUMENTS

| | | | |
|---|---|---|---|
| 4,701,613 A | 10/1987 | Watanabe et al. | |
| 5,278,425 A | 1/1994 | Bendicks et al. | |
| 5,323,637 A | 6/1994 | Bendicks et al. | |
| 5,391,891 A | 2/1995 | Wiegleb et al. | |
| 5,498,866 A | 3/1996 | Bendicks et al. | |
| 5,543,923 A * | 8/1996 | Levers et al. ................ | 356/445 |
| 5,572,017 A | 11/1996 | Veltum et al. | |
| 5,661,303 A | 8/1997 | Teder | |
| 5,898,183 A | 4/1999 | Teder | |
| 6,232,603 B1 | 5/2001 | Nelson | |
| 6,262,407 B1 | 7/2001 | Teder | |
| 6,507,015 B1 | 1/2003 | Maeno et al. | |
| 2003/0160158 A1* | 8/2003 | Ishino et al. ........... | 250/227.25 |

FOREIGN PATENT DOCUMENTS

DE        19830120 A1 *    2/1999

\* cited by examiner

*Primary Examiner*—Georgia Epps
*Assistant Examiner*—Christopher M Yealy
(74) *Attorney, Agent, or Firm*—Nixon & Vanderhye PC

(57) ABSTRACT

A raindrop sensor includes a light-emitting element, a light-receiving element and a light guide body. The light-emitting element and the light-receiving element face a transparent panel. The light guide body, which is mounted on the transparent panel, includes an input lens, an input side dividing surface, an output lens and an output side dividing surface. The input lens collimates light emitted by the light-emitting element to form an input side collimated light beam. The output lens receives the collimated light beam, which is collimated by the input lens and is reflected by a reference surface of the transparent panel, to which the raindrop attaches. The output lens converges the reflected collimated light beam toward the light-receiving element. An intersection between an imaginary extension of the input side dividing surface and an imaginary extension of the output side dividing surface is located on the reference surface of the transparent panel.

11 Claims, 5 Drawing Sheets

RAINDROP-SENSING REGION

RAINDROP-SENSING REGION

RAINDROP-SENSING REGION

RAINDROP-SENSING REGION

LOW LIGHT INTENSITY 50%

LOW LIGHT INTENSITY 50%

HIGH LIGHT INTENSITY 100%

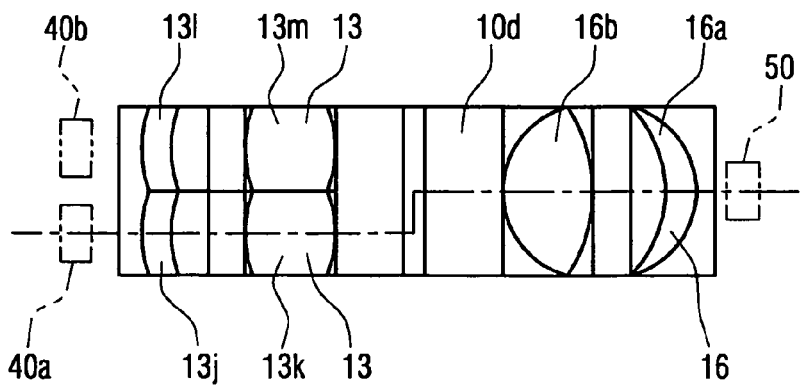
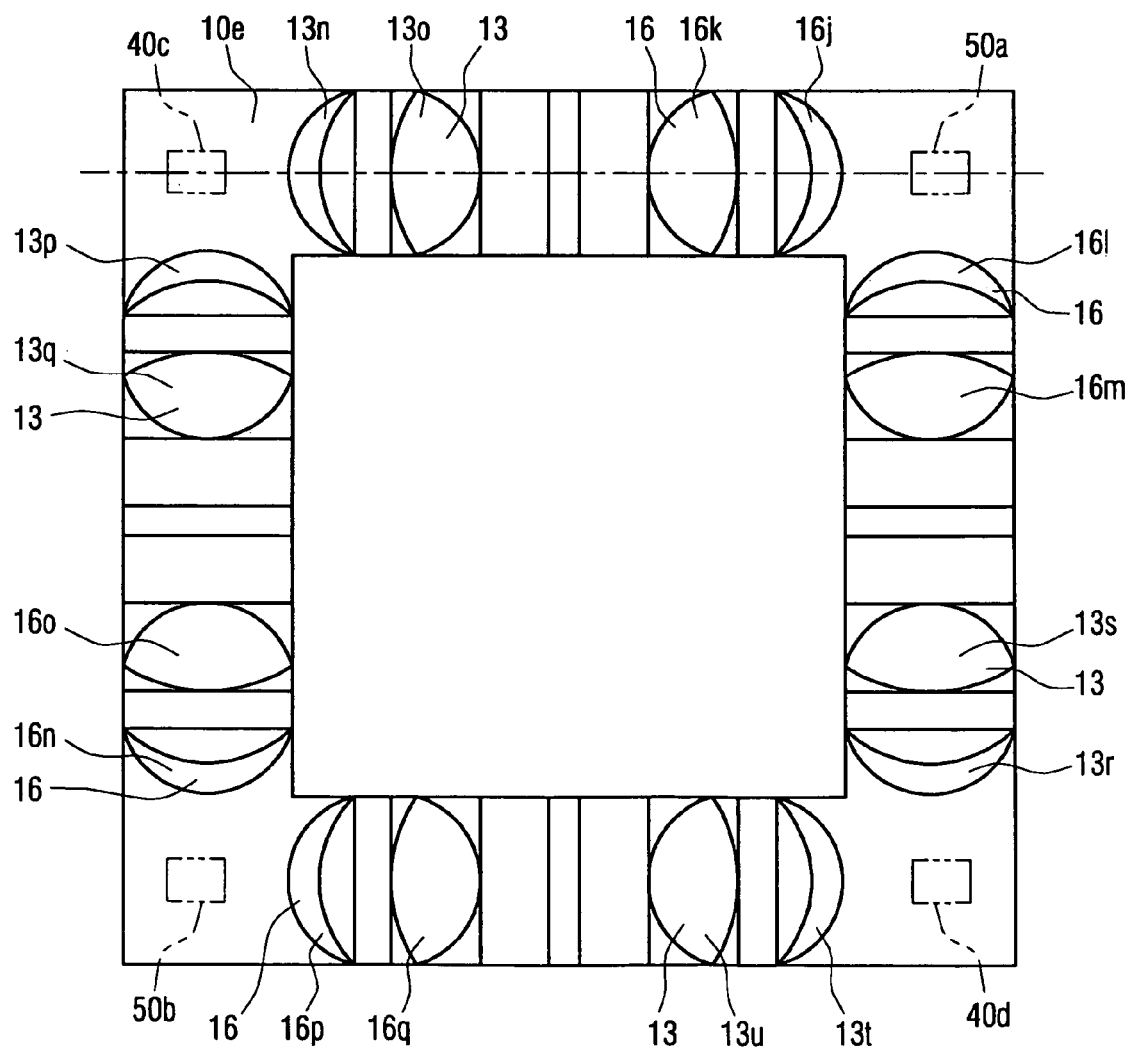

PRIOR ART

RAINDROP SENSOR

CROSS REFERENCE TO RELATED APPLICATION

This application is based on and incorporates herein by reference Japanese Patent Application No. 2004-255971 filed on Sep. 2, 2004.

BACKGROUND OF THE INVENTION

1. Field of the Invention

The present invention relates to a raindrop sensor, which is specifically suitable for a vehicle wiper automatic control device.

2. Description of Related Art

Conventionally, a raindrop sensor for detecting raindrops, which attach to a vehicle windshield and the like, is known (see Unexamined Japanese Patent Publication No. 2001-66246 corresponding to U.S. Pat. No. 6,507,015). The raindrop sensor shown in the Unexamined Japanese Patent Publication No. 2001-66246 is mounted on an interior wall of the windshield 200, and optically detects raindrop attachment as shown in FIG. 9. The raindrop sensor mainly includes a light guide body 140, planoconvex lenses 120, 130, planoconvex lens segments 150, 160, light-emitting elements 100, 110 and a light-receiving element 170.

The light guide body 140 includes inclined planes, where the planoconvex lenses 120, 130 and the planoconvex lens segments 150, 160 are formed. The planoconvex lenses 120, 130 face the light-emitting elements 100, 110. The planoconvex lens segments 150, 160 face the light-receiving element 170. A plurality of inclined planes is formed on an input side of the light guide body 140. Each of the planoconvex lenses 120, 130 is formed on a corresponding inclined plane. On the contrary, a plurality of inclined planes is formed on an output side of the light guide body 140. The planoconvex lens segments 150, 160 are formed on the corresponding plurality of inclined planes. The planoconvex lens segments 150, 160 are generated by dividing a planoconvex lens into several lens segments, a number of which is equal to that of the plurality of inclined planes.

Each light from the light-emitting elements 100, 110 is collimated to form a collimated light beam (shown by a two-dot chain line) through the planoconvex lenses 120, 130 on the input side. A predetermined region on the windshield 200 is irradiated with the collimated light beam. This region is defined as a raindrop-sensing region.

Reflecting light at the raindrop-sensing region is converged through the planoconvex lens segments 150, 160 on the output side. Then, the light-receiving element 170 receives the reflecting light to detect a raindrop amount at the raindrop-sensing region. In a structure of the above described conventional art, as shown in FIG. 9 the light from the light-emitting elements 100, 110 is applied to the planoconvex lenses 120, 130 in the input side. However, a part of the planoconvex lens 130 (around a dividing surface 180) does not receive the light from the light-emitting element 100. Therefore, an amount of light that the light guide body 140 receives is decreased, resulting in decreasing an amount of the light, which travels from the planoconvex lens 130 to the windshield 200 (shown as a shaded area in FIG. 9). As a result, accuracy for detecting raindrops is degraded at the part of the raindrop-sensing region, which receives the decreased amount of light.

Around a dividing surface 190 on the output side, in converging the reflecting light through the planoconvex lens segments 160, 150, the dividing surface 190 on the output side and the planoconvex lens 150 may limit the reflecting light from being converged in some cases. As a result, an amount of light, which travels from the windshield 200 to the planoconvex lens segment 150 (shown as a shaded area in FIG. 9), may be decreased.

SUMMARY OF THE INVENTION

The present invention addresses the above disadvantages. Thus, it is an objective of the invention to provide a raindrop sensor, which guides the light more effectively to detect raindrops more effectively.

To achieve the objective of the present invention, there is provided a raindrop sensor for sensing a raindrop attached to a transparent panel. The raindrop sensor includes a light-emitting element, a light-receiving element and a light guide body. The light-emitting element faces the transparent panel, wherein the light-emitting element emits light toward the transparent panel. The light-receiving element faces the transparent panel, wherein the light-receiving element receives the light emitted by the light-emitting element. The light guide body, which is mounted on the transparent panel, includes an input lens, an input side dividing surface, an output lens and an output side dividing surface. The input lens is formed on an input side of the light guide body, wherein the input lens is divided into a plurality of input lens segments, which are displaced from each other in a direction parallel to an optical axis of the input lens. The input side dividing surface divides adjacent two of the plurality of input lens segments and is flat. The output lens is formed on an output side of the light guide body, wherein the output lens is divided into a plurality of output lens segments, which are displaced from each other in a direction parallel to an optical axis of the output lens. The output side dividing surface divides adjacent two of the plurality of output lens segments and is flat. The input lens collimates the light, which is emitted by the light-emitting element, to form an input side collimated light beam. The output lens receives the collimated light beam, which is collimated by the input lens and is reflected by a reference surface of the transparent panel, to which the raindrop attaches. The output lens converges the reflected collimated light beam toward the light-receiving element so that the light-receiving element receives the reflected collimated light beam. An intersection between an imaginary extension of the input side dividing surface and an imaginary extension of the output side dividing surface is located on the reference surface of the transparent panel.

BRIEF DESCRIPTION OF THE DRAWINGS

The invention, together with additional objectives, features and advantages thereof, will be best understood from the following description, the appended claims and the accompanying drawings in which:

FIG. 7 is a top view for showing an arrangement of the light guide body, LED and PD according to a first modification;

FIG. 8 is a top view for showing an arrangement of the light guide body, LED and PD according to a second modification.

DETAILED DESCRIPTION OF THE INVENTION

First Embodiment

Figure 1:
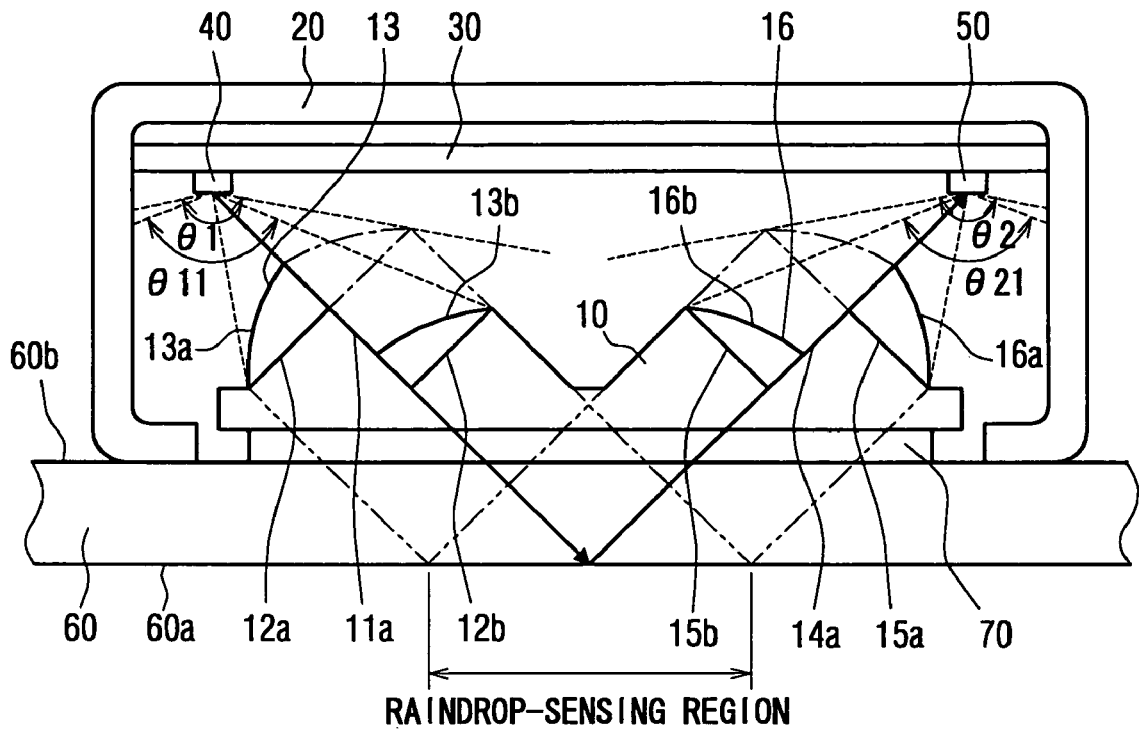
FIG. 1 is a schematic view of a light guide body taken along line I-I in FIG. 2 for showing a raindrop sensor mounted on an interior wall surface of a vehicle windshield according to a first embodiment.
Figure 2:
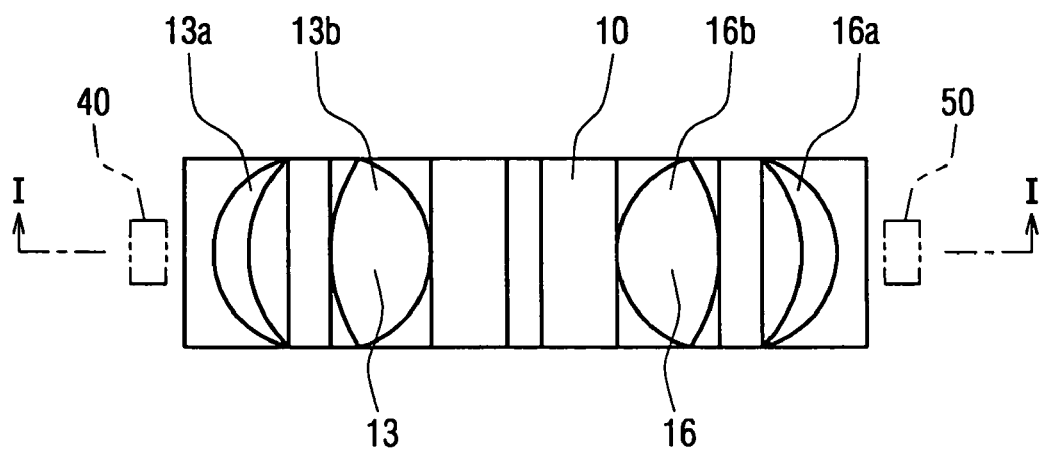
FIG. 2 is a top view for showing an arrangement of the light guide body, LED and PD as shown in FIG. 1.

A first embodiment of the present inventions will be described with reference to the accompanying drawings. A raindrop sensor is adopted for a wiper automatic control device, which is mounted on an exterior wall surface (or a reference surface) 60a of a windshield (or a transparent panel) 60 of a car. Besides the windshield, the transparent panel may include a transparent sunroof panel, a rear window, a side window or the like of the car. The raindrop sensor is mounted on an interior wall surface 60b of the windshield 60 correspondingly to a wiper area of the wiper. The raindrop sensor optically detects raindrops, which attach to the wiper area, to output a signal to the wiper automatic control device. FIG. 1 is a schematic view of a light guide body taken along line I-I in FIG. 2 for showing a raindrop sensor mounted on the interior wall surface 60b of the windshield 60 of the car according to the present invention. FIG. 2 is a top view for showing an arrangement of a light guide body 10, a light-emitting element 40 and a light-receiving element 50.

As shown in FIG. 1, the raindrop sensor includes the light guide body 10, the light-emitting element 40 and the light-receiving element 50. The light-emitting element (LED) 40 emits the light (e.g., an infrared ray) and the light is reflected by the windshield 60. Then the light-receiving element (PD) 50, such as photo diode, receives the light, which is reflected by the windshield 60. Through a process likewise, this raindrop sensor detects an amount of raindrops. Specifically, the raindrop sensor detects the amount of raindrops based on a decreased amount of light that the PD 50 receives. The amount of light is decreased because a reflectivity of the exterior wall surface 60a is changed (or decreased) due to raindrops that attach to the exterior wall surface 60a. In the raindrop sensor in the first embodiment, each LED 40 has a corresponding dedicating PD 50. A number and a combination of the LED 40 and the PD 50 may be modified. Modifications will be described later in a first modification and a second modification.

Detailed method for detecting the amount of raindrops will be described. The raindrop sensor detects the amount of raindrops by a decreasing rate. The decreasing rate is a rate between the amounts of receiving light of the PD 50 and emitting light of the LED 40. The decreasing rate is calculated by a formula, $(V_{LED} - V_{PD})/V_{LED} * 100$ (a unit is %), where the $V_{LED}$ is a voltage based on the emitting light of the LED 40, and the $V_{PD}$ is a PD output voltage. The $V_{LED}$ is also described as a corresponding output voltage of the PD 50, which corresponds to a constant current emission of the LED 40 recorded under fine weather. Also the $V_{LED}$ is described as a light-voltage converted value of the PD 50.

The light guide body 10 is located between the windshield 60 and a set of the LED 40 and the PD 50. The light guide body 10 is mounted on the interior wall surface 60b through an optical coupling layer (silicone layer) 70. The light guide body 10 leads the light from the LED 40 to the windshield 60. Then, the light guide body 10 leads the reflecting light, which is reflected by the windshield 60, to the PD 50. The light guide body 10 is generated by a resin material (e.g., polycarbonate acryl), which is optically transparent. The material that forms the light guide body 10 may alternatively be a glass material, because the material needs only to lead the light from the LED 40 to the PD 50.

The light guide body 10 includes input side inclined planes 12a, 12b and output side inclined planes 15a, 15b. The input side inclined planes 12a, 12b are inclined so that the light from the LED 40 is generally perpendicularly incident on the inclined planes 12a, 12b. The output side inclined planes 15a, 15b are inclined so that the reflecting light, which is reflected by the windshield 60, outgoes generally perpendicularly from the inclined planes 15a, 15b. Also, each inclined plane 12a, 12b, 15a, 15b does not overlap with the rest of the inclined planes 12a, 12b, 15a, 15b when the inclined planes 12a, 12b, 15a, 15b are seen in a direction perpendicular to the windshield 60.

An input lens 13 is formed on the input side inclined planes 12a, 12b, and an output lens 16 is formed on the output side inclined planes 15a, 15b. The input lens 13 collimates the light emitted from the LED 40 to form an input side collimated light beam. The output lens 16 converges a reflected collimated light beam, which is the reflecting light reflected by the windshield 60, toward the PD 50.

The input lens 13 includes a plurality of input lens segments, each of which is formed like a lens segment generated by dividing a planoconvex lens along an optical axis of the planoconvex lens. The plurality of input lens segments of the input lens 13 are described as input side planoconvex lens segments 13a, 13b. The input side planoconvex lens segment 13a is formed on the input side inclined plane 12a. The input side planoconvex lens segment 13b is formed on the input side inclined plane 12b. The output lens 16 includes a plurality of output lens segments, each of which is formed like a lens segment generated by dividing a planoconvex lens along an optical axis of the planoconvex lens. The plurality of output lens segments of the output lens 16 are described as output side planoconvex lens segments 16a, 16b. The output side planoconvex lens segment 16a is formed on the output side inclined plane 15a. The output side planoconvex lens segment 16b is formed on the input side inclined plane 15b.

The input side planoconvex lens segments 13a, 13b and the output side planoconvex lens segments 16a, 16b may be formed integrally with the light guide body 10, and may be formed separately from the light guide body 10. In a case, where the planoconvex lens segments 13a, 13b, 16a, 16b are formed separately, for example, the planoconvex lens segments 13a, 13b, 16a, 16b are attached on the corresponding inclined plane 12a, 12b, 15a, 15b with an optically transparent adhesive.

Curvatures of surfaces of the input side planoconvex lens segments 13a, 13b are defined so that the light emitted by the LED 40 is refracted to form the input side collimated light beam through the surfaces of the input side planoconvex lens segments 13a, 13b. Curvatures of surfaces of the output side planoconvex lens segments 16a, 16b are defined so that the reflected collimated light beam, which is reflected by the windshield 60, is refracted to converge toward the PD 50.

An input side dividing surface 11a divides the adjacent input side planoconvex lens segments 13a, 13b and is flat as shown in FIG. 1. The input side dividing surface 11a is generally perpendicular to the input side inclined planes 12a, 12b. Also, the input side dividing surface 11a is formed along an optical axis of the input side planoconvex lens segments 13a, 13b.

An output side dividing surface 14a divides the adjacent output side planoconvex lens segments 16a, 16b and is flat as shown in FIG. 1. The output side dividing surface 14a is generally perpendicular to the output side inclined planes 15a, 15b. Also, the output side dividing surface 14a is formed along an optical axis of the output side planoconvex lens segments 16a, 16b.

The input side dividing surface 11a and the output side dividing surface 14a are formed so that a connection between an imaginary extension of the input side dividing surface 11a and an imaginary extension of the output side dividing surface 14a is located on the exterior wall surface 60a of the windshield 60.

A circuit board 30 is held by a housing 20. The LED 40 and the PD 50 are mounted on a surface (mounting surface), which faces toward the windshield 60, of the circuit board 30. Both the LED 40 and the PD 50, which are chip type and surface-mount types, are mounted on the circuit board 30. The LED 40 applies and stops applying the light (e.g., infrared ray) to the windshield 60 within an irradiation angle θ1 (shown as dashed lines in FIG. 1), based on a driving signal from an emission driving circuit (not shown) mounted on the circuit board 30.

The PD 50 receives the reflecting light. The PD 50 receives the reflecting light, which travels within the receiving angle θ2 (shown as dashed lines in FIG. 1). Then, the PD 50 transmits a measured value of an amount of light, which the PD 50 receives, to a processing circuit (not shown) mounted on the circuit board 30. The processing circuit receives the measured value of the amount of light, and converts the measured value into a corresponding signal, which corresponds an amount of attached raindrops.

Here, the LED 40 is mounted on an intersection between the circuit board 30 and an imaginary extension of the input side dividing surface 11a. Also, the PD 50 is mounted on an intersection between the circuit board 30 and an imaginary extension of the output side dividing surface 14a.

In the present embodiment, the LED 40 and the PD 50 are surface-mount types. Therefore, mount areas are reduced so that the circuit board 30 is miniaturized. Then, the raindrop sensor is miniaturized. Also, further miniaturization of the raindrop sensor is achieved, in a case where the emission driving circuit and the processing circuit are surface-mount types.

In the present embodiment, the light guide body 10 includes two input side inclined planes 12a, 12b, and two output side inclined planes 15a, 15b. However, the light guide body 10 may have three or more inclined planes on each side. In such a case, a plurality of dividing surfaces is formed between adjacent inclined planes. One of the plurality of dividing surfaces is desirably to be formed along an optical axis of the planoconvex lens segments, which is formed on the inclined plane.

In a case where the dividing surface is not formed along the optical axis, even if the LED 40 and the PD 50 are mounted on the corresponding optical axes, irradiated areas on the windshield 60 with the light decrease. This is because more shades of ends of planoconvex lens segments are made on adjacent planoconvex lens segments, compared with a case where the dividing surface is formed along the optical axis. As a result, sensing region is more narrowed.

The input side dividing surface 11a and output side dividing surface 14a are desirable to be formed radially almost in a center of the corresponding collimated light beams. This is because in the input side, the light emitted by the LED 40 is evenly applied to the input side planoconvex lens segments 13a, 13b. This is also because in the output side, the light-receiving element receives the reflecting light effectively.

Figure 9:
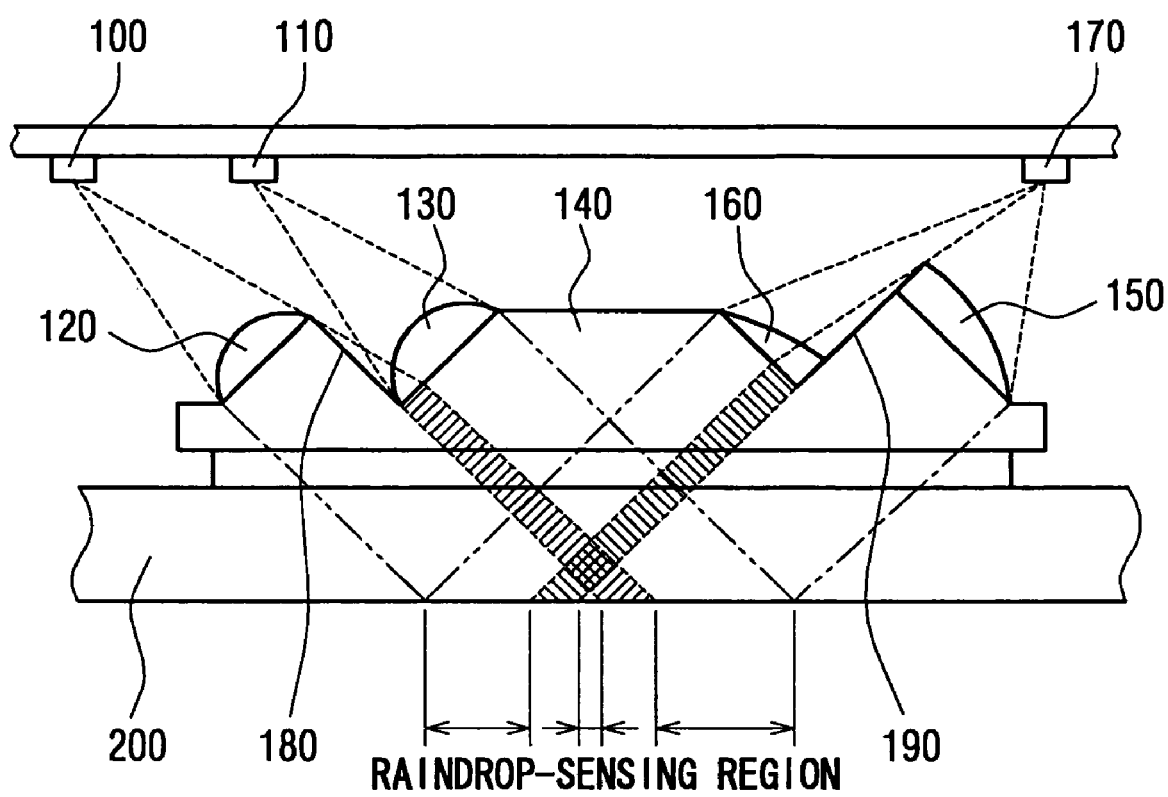
FIG. 9 a sectional view of the raindrop sensor mounted on the interior wall surface of the vehicle windshield according to a prior art.

In the present embodiment, as shown in FIG. 2, the light guide body 10 includes a group of the input side planoconvex lens segments 13a, 13b and a group of the output side planoconvex lens segments 16a, 16b. The LED 40 is mounted on the intersection between the circuit board 30 and the optical axis of the input side planoconvex lens segments 13a, 13b. Also, the PD 50 is mounted on the intersection between the circuit board 30 and the optical axis of the output side planoconvex lens segments 16a, 16b. By forming the raindrop sensor likewise, a number of components of the raindrop sensor is reduced. This is because each input side planoconvex lens segment does not require a corresponding dedicating light-emitting element that is required by each of planoconvex lenses 120, 130 as shown in the raindrop sensor of the prior art of FIG. 9.

An operation of the raindrop sensor will be described. In the present embodiment, which is composed likewise, when the LED 40 is driven by the emission driving circuit, the LED 40 emits the light (e.g., infrared ray) having a predetermined characteristic. The light is incident on surfaces of the input side planoconvex lens segments 13a, 13b. The light, which travels within an irradiation angle θ11 of the irradiation angle θ1, is incident on surfaces of the input side planoconvex lens segments 13a, 13b.

The light, which is emitted by the LED 40, is refracted to form the input side collimated light beam (shown as two-dot chain lines) through the surfaces of the input side planoconvex lens segments 13a, 13b. The input side collimated light beam travels toward the windshield 60 though the light guide body 10. The input side collimated light beam, which is collimated by the input lens 13, is applied to the exterior wall surface 60a from the interior wall surface 60b side. A region, to which the input side collimated light beam is applied, of the exterior wall surface 60a is a raindrop-sensing region.

The input side collimated light beam is reflected by the exterior wall surface 60a within the raindrop-sensing region. Thereafter, the reflecting light travels toward the output side planoconvex lens segments 16a, 16b through the light guide body 10 as the reflected collimated light beam. The reflected collimated light beam is incident on the output side planoconvex lens segments 16a, 16b, and is refracted by the surface of the output side planoconvex lens segments 16a, 16b to converge toward the PD 50 as shown by dashed lines in FIG. 1. The PD 50 receives the light, which travels within a receiving angle θ21 of the receiving angle θ2.

An optical path of the light emitted by the LED 40 is formed in above-described way. Then, in a case where the raindrops attach to the exterior wall surface 60a, the amount of the reflecting light is decreased due to the attached raindrops. Therefore, the amount of converged light converged toward the PD 50 is decreased. Then, the PD 50 transmits a first signal, which corresponds to the amount of the converged light, to the processing circuit. The processing circuit calculates the amount of the attached raindrops based on the first signal. Then, the processing circuit transmits a second signal, which corresponds to the amount of the attached raindrops, to the wiper automatic control device.

Effects of the present embodiment will be described.

(1) In a case where an intersection between an imaginary extension of an input side dividing surface and the raindrop-sensing region does not coincide with an intersection between the imaginary extension of the output side dividing surface and the raindrop-sensing region, the amount of the reflecting light is decreased due to the above-described two parts (intersections), which receives a decreased amount of light. Therefore, the amount of light may be decreased at the two parts of the raindrop-sensing region. As a result, the accuracy for detecting the raindrop at the two parts may be degraded and the amount of raindrops in the raindrop-sensing region may not be detected accurately.

In the present embodiment, the intersection between the imaginary extension of the input side dividing surface 11a and the exterior wall surface 60a coincides with the intersection between the imaginary extension of the output side dividing surface 14a and the exterior wall surface 60a. Therefore, the raindrop-sensing region becomes to have a single part (intersection), which receives the decreased amount of light. Thus, it is possible to reduce a number of a part, where the accuracy for sensing the raindrop is degraded.

The reason for the decrease of the amount of light will be described. On the input side of the light guide body, the input side dividing surface is formed between each input side planoconvex lens segments and corresponding input side inclined planes. Because of the input side dividing surface, the less amount of light reaches to the intersection between the imaginary extension of the input side dividing surface and the raindrop-sensing region.

Also, on the output side of the light guide body, the output side dividing surface is formed between output side planoconvex lens segments and corresponding output side inclined planes. The amount of light for the reflecting light is reduced at a corresponding part on the raindrop-sensing region, which corresponds to the intersection between the imaginary extension of the output side dividing surface and the raindrop-sensing region. In other words, at the intersection between the imaginary extension of the output side dividing surface and the raindrop-sensing region, the raindrop-sensing region receives a less amount of light.

(2) As shown in FIG. 1, the light guide body 10 includes the inclined planes 12a, 12b on the input side, and the inclined planes 15a, 15b on the output side. Also, the light guide body 10 includes the dividing surface 11a between the inclined planes 12a, 12b on the input side, and the dividing surface 14a between the inclined planes 15a, 15b on the output side. In other words, because the inclined planes 12a, 12b, 15a, 15b, which are formed on the input side and the output side of the light guide body 10, are formed into steps, the height of the light guide body 10 is smaller than that of a conventional light guide body (shown as chain lines).

(3) The input side planoconvex lens segments 13a, 13b, which are generated by dividing a planoconvex lens into two lens segments, are formed on the corresponding input side inclined planes 12a, 12b of the light guide body 10. The output side planoconvex lens segments 16a, 16b, which are generated by dividing a planoconvex lens into two lens segments, are formed on the corresponding output side inclined planes 15a, 15b of the light guide body 10. Thus, a single optical axis is formed on the input side, and a single optical axis is formed on the output side. Therefore, a number of the LED 40 and the PD 50 is less than that of the conventional raindrop sensor.

(4) In a case, where the planoconvex lens is divided into two lens segments, it is desirable to divide the planoconvex lens along the optical axis of the planoconvex lens. In a case, where the planoconvex lens is not divided along the optical axis of the planoconvex lens, the input side planoconvex lens segment is shadowed with an end of the corresponding adjacent input side planoconvex lens segment, when the LED 40 is located on the imaginary extension of the optical axis of the planoconvex lens. Also the output side planoconvex lens segment is shadowed with an end of the corresponding adjacent output side planoconvex lens segment, when the PD 50 is located on the imaginary extension of the outgoing optical axis of the planoconvex lens.

(5) A radial center of the input side collimated light beam, which is collimated by the input lens 13, is generally located in the input side dividing surface 11a. A radial center of the reflected collimated light beam, which is collimated by the input lens 13 and is reflected by the reference surface 60a of the windshield 60, is generally located in the output side dividing surface 14a. Therefore, in the input side, the light emitted by the LED 40 reaches evenly to the input side planoconvex lens segments 13a, 13b. Also, in the output side, the reflecting light is effectively received by the light-receiving element.

(6) Each of the inclined planes 12a, 12b, 15a, 15b on the input side and the output side is formed in a way where projected images of each inclined plane on the windshield 60 do not overlap with each other. Thus, the thickness of the light guide body 10 becomes even. Likewise, a sink mark and a void are limited from forming, while the light guide body 10 is molded. Also, a production unit of the light guide body 10 does not need a device to limit a maldistribution of temperature. Thus, a production cost of the light guide body 10 is limited from increasing.

(7) The LED 40, which is formed on the circuit board 30, is located at the intersection between the circuit board 30 and the imaginary extension of the input side dividing surface 11a. The PD 50, which is formed on the circuit board 30, is located at the intersection between the circuit board 30 and the imaginary extension of the output side dividing surface 14a. Therefore, shadows due to the light guide body 10 and lenses are limited from being produced in a process where the LED 40 emits the light toward the input side planoconvex lens segments 12a, 12b, and the reflected collimated light beam, which is reflected by the windshield 60, is converged by the output side planoconvex lens segments 16a, 16b.

(8) A radial center of the input side collimated light beam, which is collimated by the input lens 13, is generally located in the input side dividing surface 11a. A radial center of the reflected collimated light beam, which is collimated by the input lens 13 and is reflected by the reference surface 60a of the windshield 60, is generally located in the output side dividing surface 14a. Therefore, in the input side, the light emitted by the LED 40 reaches evenly to the input side planoconvex lens segments 13a, 13b. Also, in the output side, the reflected collimated light beam is converged by both the output side planoconvex lens segments 16a, 16b toward the PD 50.

Figure 6:
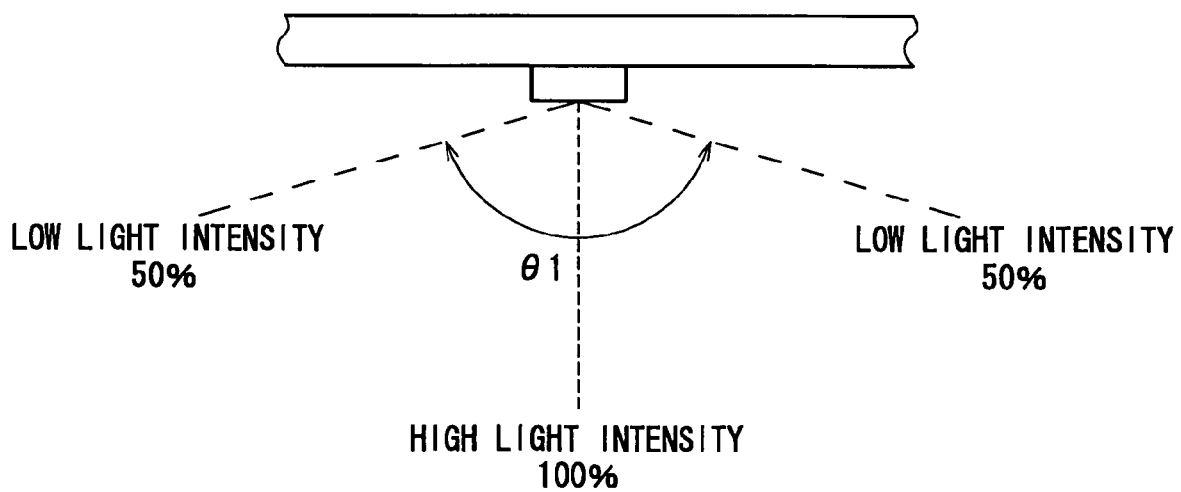
FIG. 6 shows a relationship between a light irradiation angle and a light intensity of LED.

(9) For example, as shown in FIG. 6, the LED 40 emits the light with a directivity, whereby the light travels within the irradiation angle θ1 of 120°. If the amount of light around the radial center of the LED 40 were 100%, the amount of light at a radially outer peripheral of the light ray (shown as dashed lines in FIG. 6) would be about 50%. According to the present embodiment as shown in FIG. 1, the input side inclined planes 12a, 12b, on which the input side planoconvex lens segments 13a, 13b are respectively formed, are formed into step shapes. Thus, the light within the irradiation angle θ11, which has stronger light intensity, is selectively used from the light within the predetermined irradiation angle θ1 of the LED 40.

The PD 50 has a predetermined light-receiving angle θ2. A light-receiving rate at a radially outer peripheral of the light ray is lower than that at a radial center of the light. In the present embodiment, the output side inclined planes 15a, 15b, on which the output side planoconvex lens segments 16a, 16b are respectively formed, are formed into step shapes. Thus, the light-receiving angle θ21, which has more efficient receiving rate, is selectively used from the predetermined light-receiving angle θ2 of the PD 50.

(10) A distance between the circuit board 30 and the light guide body 10 is adjusted to be shorter in order to make an effective use of the predetermined irradiation angle θ1, within which the LED 40 emits the light, and the predetermined light-receiving angle θ2, within which the PD 50 receives the light. Then, it is possible to make the raindrop sensor thinner.

(11) The predetermined irradiation angle, within which the LED 40 emits the light, and the predetermined light-receiving angle, within which the PD 50 receives the light may be narrowed.

(12) Curvatures of surfaces of the input side planoconvex lens segments 13a, 13b are defined so that the light emitted by the LED 40 is collimated to form the input side collimated light beam through the surfaces of the input side planoconvex lens segments 13a, 13b. Curvatures of surfaces of the output side planoconvex lens segments 16a, 16b are defined so that the reflected collimated light beam, which is reflected by the windshield 60, is refracted to converge toward the PD 50.

Therefore, the input side and reflected collimated light beams can be formed in the light guide body 10 and the reflected collimated light beam can be converged to the PD 50 even in a condition, where a distance between the LED 40 and the input side planoconvex lens segment 13a is different from a distance between the LED 40 and the input side planoconvex lens segment 13b, also a distance between the PD 50 and the output side planoconvex lens segment 16a is different from a distance between the PD 50 and the output side planoconvex lens segment 16b.

Second Embodiment

Figure 3:
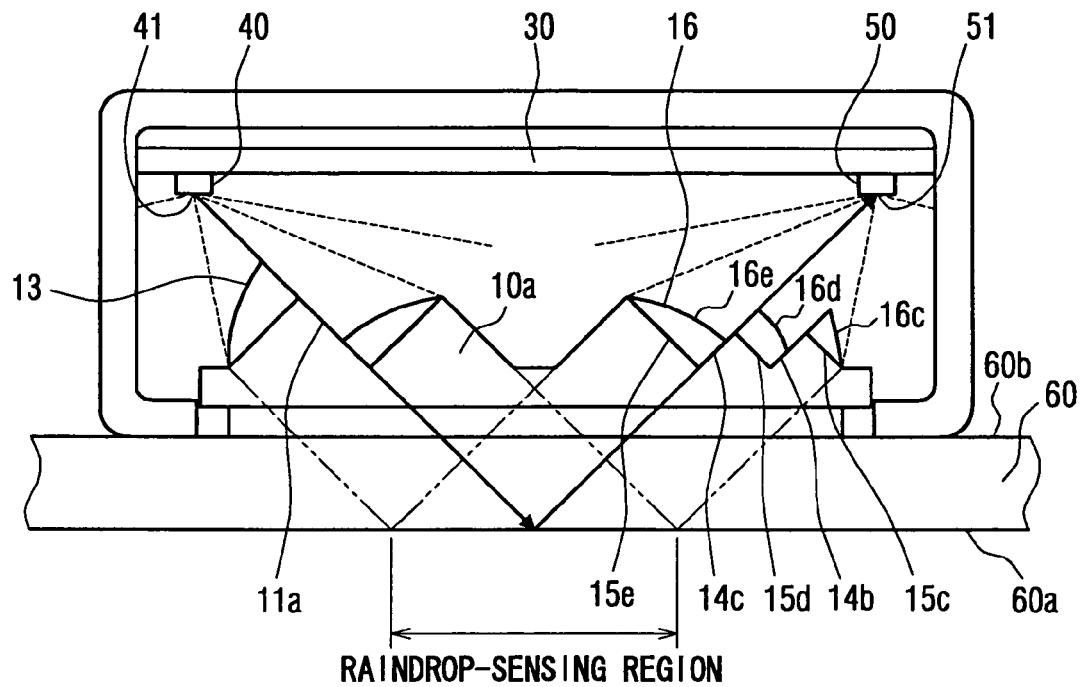
FIG. 3 is a sectional view of the raindrop sensor mounted on the interior wall surface of the vehicle windshield according to a second embodiment.
Figure 4:
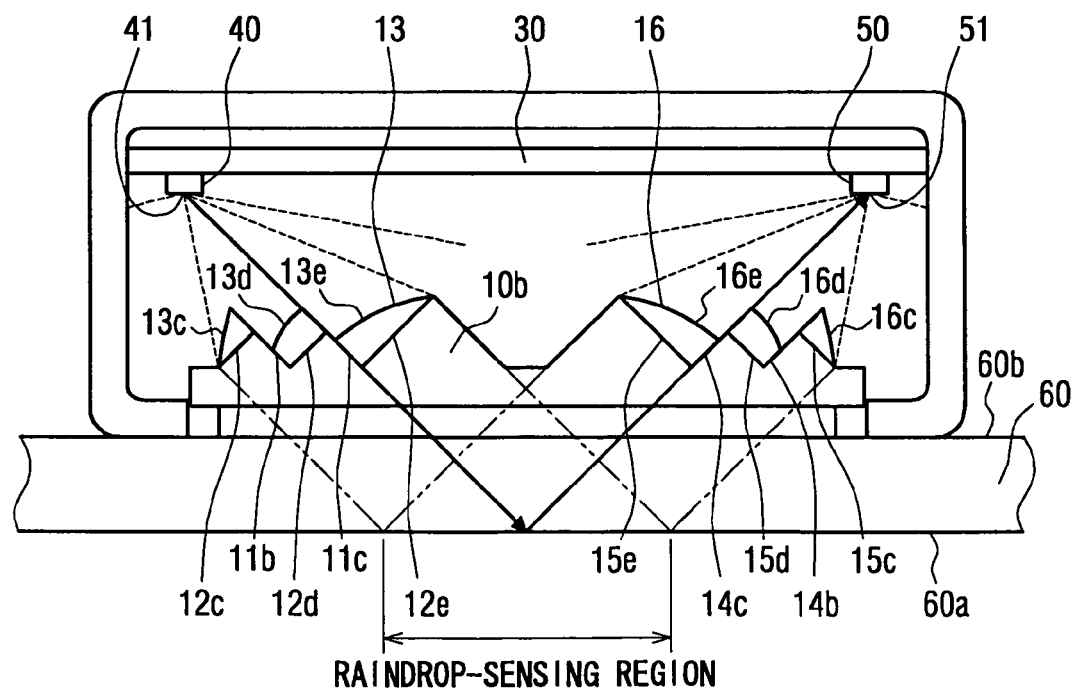
FIG. 4 is a sectional view of the raindrop sensor mounted on the interior wall surface of the vehicle windshield according to a modification of the second embodiment.

A second embodiment of the present invention will be described with reference to FIG. 3 and FIG. 4. Similar components of the raindrop sensor of the second embodiment, which is similar to the components of the raindrop sensor of the first embodiment, will be indicated by the same numerals. In the second embodiment, three or more of inclined planes are formed on at least one of the input side and output side. FIG. 3 is a sectional view of the raindrop sensor mounted on the interior wall surface 60b of the windshield 60 of the car according to the second embodiment. FIG. 4 is a sectional view of the raindrop sensor mounted on the interior wall surface 60b of the windshield 60 of the car according to a modification of the second embodiment.

As shown in FIG. 3, the light guide body 10a includes three output side inclined planes 15c-15e and two output side dividing surfaces 14b, 14c. Output side planoconvex lens segments 16c-16e are formed on the corresponding output side inclined planes 15c-15e. The output side dividing surface 14b is formed between the output side inclined planes 15c and 15d, and the output side dividing surface 14c is formed between the output side inclined planes 15d and 15e. An intersection between an imaginary extension of the input side dividing surface 11a and an imaginary extension of the output side dividing surface 14c is located on the exterior wall surface 60a of the windshield 60.

Also, a light-receiving point 51 of the PD 50 is mounted on an intersection of the mounting surface of the circuit board 30 and the imaginary extension of the output side dividing surface 14c. The outgoing inclined plane 15e is formed on the LED 40 side of the output side dividing surface 14c. The outgoing inclined planes 15c, 15d are formed on the other side of the output side dividing surface 14c.

As shown in FIG. 4, the light guide body 10b includes three input side inclined planes 12c-12e and two input side dividing surfaces 11b, 11c on the input side. Also, the light guide body 10b includes three output side inclined planes 15c-15e and two output side dividing surfaces 14b, 14c. Input side planoconvex lens segments 13c-13e are formed on the corresponding input side inclined planes 12c-12e. The input side dividing surface 11b is formed between the input side inclined planes 12c and 12d, and the input side dividing surface 1c is formed between the input side inclined planes 12d and 12e. The inclined planes, the dividing surfaces and the planoconvex lens segments on the output side coincide with those shown in FIG. 3.

An intersection between an imaginary extension of the input side dividing surface 11c and an imaginary extension the output side dividing surface 14c is located on the exterior wall surface 60a of the windshield 60. Also, a light emitting point 41 of the LED 40 is mounted on an intersection between the mounting surface of the circuit board 30 and the imaginary extension of the input side dividing surface 11c. The incoming inclined plane 12e is formed on the PD 50 side of the input side dividing surface 11c. The incoming inclined planes 12c, 12d are formed on the other side of the input side dividing surface 11c.

Effects of the present embodiment will be described.

(1) In a case where three or more of the input side inclined planes are formed, a single first radial side lens segment 13e, which is furthest from the light-emitting element 40 among the plurality of input lens segments 13c-13e, is located on a first radial side of the optical axis of the input lens 13. Also, a plurality of second radial side lens segments 13c, 13d, which is closer to the light-emitting element 40 relative to the single first radial side lens segment 13e, is located on a second radial side of the optical axis of the input lens 13. Likewise, each planoconvex lens segment is not shaded with a corresponding adjacent inclined plane and a corresponding adjacent planoconvex lens segment, and a thickness of the light guide body 10b can become even.

(2) In a case where three or more of the output side inclined planes are formed, an output side inclined plane 15e is formed on the LED 40 side of the output side dividing surface 14c. The PD 50 is located on the extension of the output side dividing surface 14c. Also, the output side inclined planes 15c, 15d are formed on the other side of the output side dividing surface 14c. Likewise, the light emitted from each planoconvex lens segment is limited from being blocked by a corresponding adjacent inclined plane and a corresponding adjacent planoconvex lens segment, and a thickness of the light guide body 10a can become even.

Third Embodiment

Figure 5:
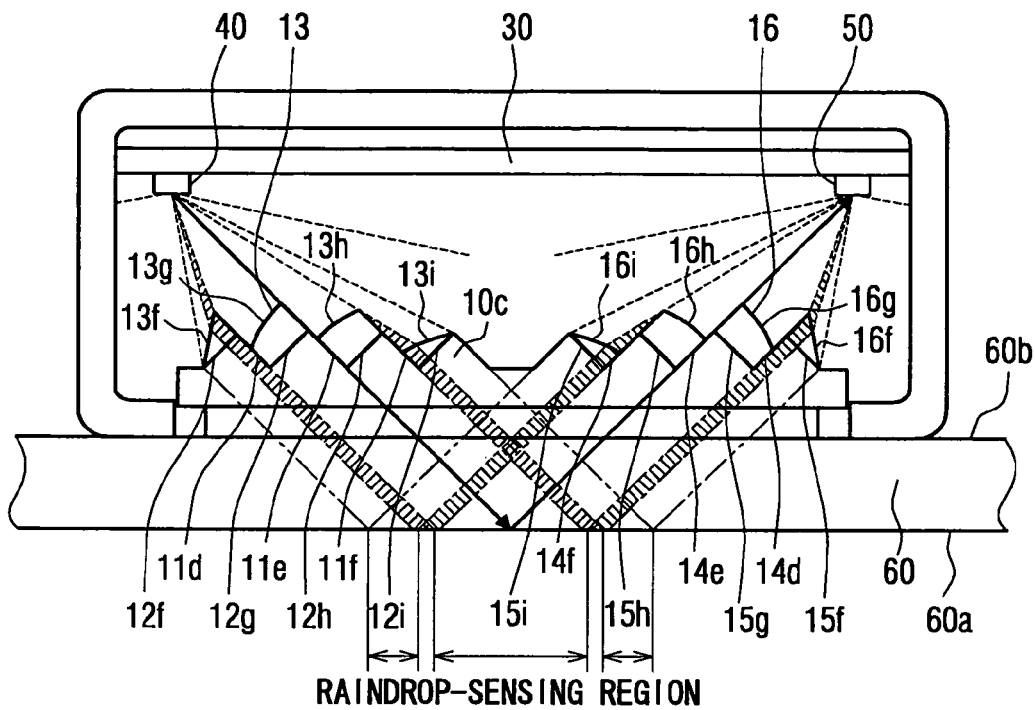
FIG. 5 is a sectional view of the raindrop sensor mounted on the interior wall surface of the vehicle windshield according to a third embodiment.

A comparative example will be described with reference to FIG. 5. Similar components of the raindrop sensor of the third embodiment, which is similar to the components of the raindrop sensor of the first and/or second embodiments, will be indicated by the same numerals. In the comparative example four input side inclined planes and four output side inclined planes are formed. FIG. 5 is a sectional view of the raindrop sensor mounted on the interior wall surface 60b of the windshield 60 of the car according to the third embodiment. As shown in FIG. 5, the light guide body 10c includes four input side inclined planes 12f-12i and three input side dividing surfaces 11d-11f on the input side. Also, the light guide body 10c includes four output side inclined planes 15f-15i and three output side dividing surfaces 14d-14f. Input side planoconvex lens segments 13f-13i are formed on the corresponding input side inclined planes 12f-12i. Output side planoconvex lens segments 16f-16i are formed on the corresponding output side inclined planes 15f-15i.

An intersection between an imaginary extension of the input side dividing surface 11e and an imaginary extension of the output side dividing surface 14e is located on the exterior wall surface 60a of the windshield 60. Further, the LED 40 is located at an intersection between the mounting surface of the circuit board 30 and the imaginary extension of the input side dividing surface 11e. Also, the PD 50 is located at an intersection between the mounting surface of the circuit board 30 and the imaginary extension of the output side dividing surface 14e.

Effects of the present embodiment will be described. The light guide body 10c can be made thinner than those in any other embodiments and the thickness of the light guide body 10c can become even. This is because the light guide body 10c includes four inclined planes on the input side, and four inclined planes on the output side.

A first modification will be described with reference to FIG. 7. As shown in FIG. 7, a light guide body 10d includes two groups of input side planoconvex lens segments and a group of output side planoconvex lens segments 16a, 16b. A first input lens 13 includes input side planoconvex lens segments 13j, 13k. A second input lens 13 includes input side planoconvex lens segments 13l, 13m. The output side planoconvex lens segments and the PD 50 in the present embodiment coincide with those in the first embodiment. Thus, the output side planoconvex lens segments and the PD 50 are indicated by the corresponding numerals, which are used in the first embodiment.

As shown in FIG. 7, the first and second input lenses, which includes the input side planoconvex lens segments 13j-13m, are formed on the light guide body 10d so that an optical axis of the first input lens 13, which includes the input side planoconvex lens segments 13j, 13k, is parallel to an optical axis of the second input lens 13, which includes the input side planoconvex lens segments 13l, 13m. Each of LEDs 40a, 40b are located at intersections between the circuit board 30 and the corresponding optical axes. A width of each of the input side planoconvex lens segments 13j-13m is about a half of that of each of the output side planoconvex lens segments 16a, 16b.

Light emitted by the LED 40a is applied to about a half of the region of the raindrop-sensing region through the first input lens 13, which includes the input side planoconvex lens segments 13j, 13k. Light emitted by the LED 40b is applied to the other half of the raindrop-sensing region through the second input lens 13, which includes the input side planoconvex lens segments 13l, 13m. The LED 40a and the LED 40b are made to alternately emit the light by a driving circuit (not shown). The PD 50 receives the light, which are alternately emitted from the LEDs 40a, 40b. The raindrop sensor detects the amount of raindrops based on the decreasing rate of the amount of received light compared with the amount of the emitted light.

According to the first modification, which includes the above-described structure, the raindrop-sensing region is divided into two regions and each decreasing rate of the amount of received light compared with the amount of the emitted light for a corresponding raindrop-sensing region is calculated separately. Therefore, compared with a case where the raindrop-sensing region is not divided, even a small amount of raindrops can be described as a larger decreasing rate of the amount of the received light. Thus, the accuracy for detecting the raindrops is improved.

The second modification will be described with reference to FIG. 8. A light guide body 10e includes four input lenses 13, which include input side planoconvex lens segments 13n-13u, and four output lenses 16, which include output side planoconvex lens segments 16j-16q. Also, two LEDs 40c, 40d and two PDs 50a, 50b are mounted on the circuit board 30.

As shown in FIG. 8, the light guide body 10e is shaped into a generally foursquare, when seen from a top. Each side of the generally foursquare of the light guide body 10e includes a corresponding one of the four input lenses 13, which include the input side planoconvex lens segments 13n-13u, and a corresponding one of the four output lenses 16, which include the output side planoconvex lens segments 16j-16q. A first input lens 13, which includes the input side planoconvex lens segments 13n, 13o and a second input lens 13, which includes the input side planoconvex lens segments 13p, 13q, are located so that an intersection between an optical axis of the first input lens 13 and an optical axis of the second input lens 13 is located around a first corner portion of the light guide body 10e. A third input lens 13, which includes the input side planoconvex lens segments 13s, 13r and a fourth input lens 13, which includes the input side planoconvex lens segments 13t, 13u, are located so that an intersection between an optical axis of the third input lens 13 and an optical axis of the fourth input lens 13 is located around a second corner portion, which is located on a diagonal position of the first corner portion, of the light guide body 10e.

A first output lens 16, which includes the output side planoconvex lens segments 16j, 16k, and a second output lens 16, which includes the output side planoconvex lens segments 16l, 16m, are located so that an intersection between an optical axis of the first output lens 16 and an optical axis of the second output lens 16 is located around a third corner portion, which is different from the above-described first and second corner portions, of the light guide body 10e. A third output lens 16, which includes the output side planoconvex lens segments 16n, 16o, and a fourth output lens 16, which includes the output side planoconvex lens segments 16p, 16q, are located so that an intersection between an optical axis of the third output lens 16 and an optical axis of the fourth output lens 16 is located around a fourth corner portion, which is located on a diagonal position of the third corner portion, of the light guide body 10e.

The LEDs 40c, 40d and the PDs 50a, 50b are mounted on the circuit board 30. The LED 40c is located at the intersection between the optical axis of the first input lens 13 and the optical axis of the second input lens 13. The LED 40d is located at the intersection between the optical axis of the third input lens 13 and the optical axis of the fourth input lens 13. The PD 50a is located at the intersection between the optical axis of the first output lens 16 and the optical axis of the second output lens 16. The PD 50b is located on an intersection between the optical axis of the third output lens 16 and the optical axis of the fourth output lens 16.

In the above-described structure, the four input lenses 13, which includes the input side planoconvex lens segments 13n-13u, and the four output lenses 16, which includes the output side planoconvex lens segments 16j-16q, are formed on the light guide body 10e. However, only two LEDs 40c, 40d and only two PDs 50a, 50b are needed to be mounted on the circuit board 30. Thus, a number of the LEDs and the PDs are reduced compared with that of the input lenses and output lenses, and a broader raindrop-sensing region can still be covered. Alternatively, the input lenses 13, which includes the input side planoconvex lens segments 13n-13q, and the output lenses 16, which includes the output side planoconvex lens segments 16j, 16k, 16n, 16o, may be located in an L form in order to reduce a number of at least one of the LEDs and the PDs. The number of the LED and the PD is reduced, because the at least one of the LED or the PD can be shared.

The transparent panel is not limited to the windshield of the vehicle. The transparent panel is alternatively the transparent sunroof panel, the side window, the rear window and the like.

Additional advantages and modifications will readily occur to those skilled in the art. The invention in its broader terms is therefore not limited to the specific details, representative apparatus, and illustrative examples shown and described.

What is claimed is:

1. A raindrop sensor for sensing a raindrop attached to a transparent panel, the raindrop sensor comprising:
   a light-emitting element, which faces the transparent panel, wherein the light-emitting element emits light toward the transparent panel;
   a light-receiving element, which faces the transparent panel, wherein the light-receiving element receives the light emitted by the light-emitting element;
   a light guide body, which is mounted on the transparent panel, wherein the light guide body includes:
      an input lens, which is formed on an input side of the light guide body, wherein the input lens is divided into a plurality of input lens segments, which are displaced from each other in a direction parallel to an optical axis of the input lens;
      an input side dividing surface, which divides adjacent two of the plurality of input lens segments and is flat;
      an output lens, which is formed on an output side of the light guide body, wherein the output lens is divided into a plurality of output lens segments, which are displaced from each other in a direction parallel to an optical axis of the output lens; and
      an output side dividing surface, which divides adjacent two of the plurality of output lens segments and is flat, wherein: the input lens collimates the light, which is emitted by the light-emitting element, to form an input side collimated light beam;
   the output lens receives the collimated light beam, which is collimated by the input lens and is reflected by a reference surface of the transparent panel, to which the raindrop attaches;
   the output lens converges the reflected collimated light beam toward the light-receiving element so that the light-receiving element receives the reflected collimated light beam;
   an intersection between an imaginary extension of the input side dividing surface and an imaginary extension of the output side dividing surface is located on the reference surface of the transparent panel; wherein
   the input side dividing surface extends along the optical axis of the output lens;
   the output side dividing surface extends along the optical axis of the output lens; and
   at least one of the plurality of input lens segments and the plurality of output lens segments includes:
      a single first radial side lens segment, which is located on a first radial side of the optical axis of a corresponding one of the input lens and the output lens is furthest from a corresponding one of the light-emitting element and the light-receiving element among the at least one of the plurality of input lens segments and the plurality of output lens segments; and
      a plurality of second radial side lens segments, which is located on a second radial side of the optical axis of the corresponding one of the input lens and the output lens and is closer to the corresponding one of the light-receiving element and the light-receiving element relative to the single first radial side lens segment.

2. The raindrop sensor according to claim 1, wherein:
   the plurality of input lens segments is a plurality of input side planoconvex lens segments generated by dividing an input side planoconvex lens into a plurality of lens segments;
   an output side plane of each input side planoconvex lens segment is an inclined plane, which is inclined relative to the reference surface;
   the plurality of output lens segments is a plurality of output side planoconvex lens segments generated by dividing an output side planoconvex lens into a plurality of lens segments; and
   an input side plane of each output side planoconvex lens segment is an inclined plane, which is inclined relative to the reference surface.

3. The raindrop sensor according to claim 2, wherein each inclined plane does not overlap with the rest of the inclined planes, when the inclined planes are seen in a direction perpendicular to the transparent panel.

4. The raindrop sensor according to claim 2, wherein:
   curvatures of surfaces of the plurality of input side planoconvex lens segments are defined so that the light emitted by the light-emitting element is collimated to form the input side collimated light beam on the input side of the light guide body; and
   curvatures of surfaces of the plurality of output side planoconvex lens segments are defined so that the reflected collimated light beam is converged toward the light-receiving element.

5. The raindrop sensor according to claim 2, further comprising:
   a circuit board, on which the light-emitting element and the light-receiving element are mounted, wherein the light-emitting element is a first light-emitting element; and
   a second light-emitting element, which is mounted on the circuit board, wherein:
   the input lens is a first input lens, which includes the plurality of input side planoconvex lens segments;
   the light guide body further includes a second input lens, which includes a plurality of input side planoconvex lens segments;

an optical axis of the first input lens is parallel to an optical axis of the second input lens;

the first light-emitting element is located at an intersection between the circuit board and the optical axis of the first input lens;

the second light-emitting element is located at an intersection between the circuit board and the optical axis of the second input lens; and the light-receiving element is located at an intersection between the circuit board and the optical axis of the output lens.

6. The raindrop sensor according to claim 2, wherein:

the input lens is a first input lens, which includes the plurality of input side planoconvex lens segments;

the light guide body further includes a second input lens, which includes the plurality of input side planoconvex lens segments;

the output lens is a first output lens, which includes the plurality of output side planoconvex lens segments;

the light guide body further includes a second output lens, which includes a plurality of output side planoconvex lens segments; and the first and second input lenses and the first and second output lenses are located to satisfy at least one of the following conditions:

the light-emitting element is located at an intersection between an optical axis of the first input lens and an optical axis of the second input lens; and the light-receiving element is located at an intersection between an optical axis of the first output lens and an optical axis of the second output lens.

7. The raindrop sensor according to claim 1, further comprising a circuit board, on which the light-emitting element and the light-receiving element are mounted, wherein:

the light-emitting element is located on an intersection between the circuit board and the imaginary extension of the input side dividing surface; and the light-receiving element is located on an intersection between the circuit board and the imaginary extension of the output side dividing surface.

8. The raindrop sensor according to claim 1, wherein:

a radial center of the input side collimated light beam, which is collimated by the input lens, is located in the input side dividing surface; and a radial center of the reflected collimated light beam, which is collimated by the input lens and is reflected by the reference surface of the transparent panel, is located in the output side dividing surface.

9. The raindrop sensor according to claim 1, wherein said at least one of the plurality of input lens segments and the plurality of output lens segments is the plurality of input lens segments;

said corresponding one of the input lens and the output lens is the input lens; and said corresponding one of the light-emitting element and the light-receiving element is the light-emitting element.

10. The raindrop sensor according to claim 1, wherein said at least one of the plurality of input lens segments and the plurality of output lens segments is the plurality of output lens segments;

said corresponding one of the input lens and the output lens is the output lens; and said corresponding one of the light-emitting element and the light-receiving element is the light-receiving element.

11. The raindrop sensor according to claim 1, wherein:

the light-emitting element is located generally on the imaginary extension of the input side dividing surface in a direction away from said transparent panel; and the light-receiving element is located generally on the imaginary extension of the output side dividing surface in a direction away from said transparent panel.

* * * * *